US007262326B2

(12) United States Patent
Blanchet et al.

(10) Patent No.: US 7,262,326 B2
(45) Date of Patent: Aug. 28, 2007

(54) PROCESS FOR THE SYNTHESIS OF INDANYLAMINE OR AMINOTETRALIN DERIVATIVES AND NOVEL INTERMEDIATES

(75) Inventors: Sylvie Blanchet, Feneu (FR); Bertrand Blandine, Angrie (FR); Alain Burgos, les-Ponts-de-Ce (FR); Yvon Derrien, la Meignanne (FR); Marie-Laure Moreau, Bourgneuf-en-Mauges (FR)

(73) Assignee: Teva Pharmaceuticals Industries Ltd., Petach Tikva (IL)

( * ) Notice: Subject to any disclaimer, the term of this patent is extended or adjusted under 35 U.S.C. 154(b) by 0 days.

(21) Appl. No.: 11/221,035

(22) Filed: Sep. 7, 2005

(65) Prior Publication Data

US 2006/0052639 A1    Mar. 9, 2006

Related U.S. Application Data

(60) Provisional application No. 60/607,881, filed on Sep. 8, 2004.

(51) Int. Cl.
*C07C 233/05* (2006.01)
(52) U.S. Cl. .................. 564/219; 564/221; 564/222; 564/305; 560/129
(58) Field of Classification Search ............... 564/219, 564/221, 222, 305; 560/129
See application file for complete search history.

(56) References Cited

FOREIGN PATENT DOCUMENTS

| WO | WO98/27055 | 6/1998 |
|----|------------|--------|
| WO | WO 00/38673 | 7/2000 |
| WO | WO 2005/063687 A2 | 7/2005 |
| WO | WO 2005/082838 A1 | 9/2005 |

OTHER PUBLICATIONS

Anilkumar et al, Tetrahedron Letters(41), 2000, 5427-5429.*
Sterling et al, J. Med.Chem. 2002, 45, 5260-6279.*
Gan, P. et al., "Synthesis of Indanones and Tetralones as New Potential Schistosomicidals," *Acta Pharmaceutica Sinica*, vol. 20, No. 5, pp. 345-352 (1985) (English language abstract is on p. 352).
Oshiro et al., J. Med. Chem. 1991, 34, 2004-2013, "Novel Cerebroprotective Agents with Central Nervous System Stimulating Activity. 1. Synthesis and Pharmacology of 1-Amino-7-hydrozyindan Derivatives" © American Chemical Society.
March's Advanced Organic Chemistry; Michael B. Smith & Jerry March, 5th Edition, chapter 10, section 10-11, 2001
March's Advanced Organic Chemistry; Michael B. Smith & Jerry March, 5th Edition p. 1194, 2001.

* cited by examiner

*Primary Examiner*—Shailendra Kumar
(74) *Attorney, Agent, or Firm*—Merchant & Gould P.C.

(57) ABSTRACT

A process for preparing indanylamine and aminotetralin derivatives from indanone or tetralone oximes by acylating the oximes with an organic anhydride, followed by catalytic hydrogenation in the presence of an organic anhydride with subsequent hydrolysis is described. The process is commercially feasible providing indanylamine and aminotetralin derivatives in high yield that are useful as intermediates in the production of therapeutically active compounds. Also described are novel intermediates, 1-indanone O-acetyl oximes and 1-tetralone O-acetyl oximes.

26 Claims, No Drawings

PROCESS FOR THE SYNTHESIS OF INDANYLAMINE OR AMINOTETRALIN DERIVATIVES AND NOVEL INTERMEDIATES

This application claims benefit of 60/607,881, filed Sep. 8, 2004.

FIELD OF THE INVENTION

This invention relates to processes for preparation of indanylamine or aminotetralin derivatives. In addition, this invention relates to intermediates which can be used in the preparation of indanylamine or aminotetralin derivatives.

BACKGROUND OF THE INVENTION

Indanylamine and aminotetralin derivative compounds, such as those of Formula I below, are useful to treat depression, Attention Deficit Disorder (ADD), Attention Deficit and Hyperactivity Disorder (ADHD), Tourett's Syndrome, Alzheimer's Disease and other dementias as described in PCT application publication 98/27055. The indanylamine derivatives disclosed have been shown to have biological effects in animal models of neurological disease.

Formula I is:

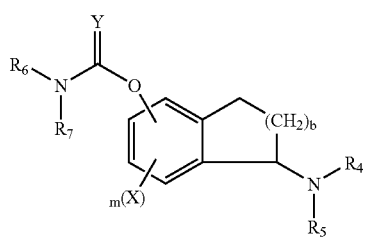

(I)

wherein b is 1 or 2; m is from 0-3, Y is O or S, X is halo, $R_4$ is hydrogen or $C_{1-4}$ alkyl, $R_5$ is hydrogen, $C_{1-4}$ alkyl, or optionally substituted propargyl and $R_6$ and $R_7$ are each independently hydrogen, $C_{1-8}$ alkyl, $C_{6-12}$ aryl, $C_{6-12}$ aralkyl, each optionally halo substituted.

PCT application publication 98/27055 further discloses methods for the preparation of indanylamine and aminotetralin derivatives of Formula I using, for example, as starting materials 3-amino-indan-5-ol or 6-methoxy-1-aminoindan. Methods of preparation of the starting materials are also disclosed. 6-Methoxy-indan-1-ylamine is prepared by conversion of 6-methoxy-indan-1-one to 6-methoxy-indan-1-one oxime followed by reduction to 6-methoxy-indan-1-ylamine. Alternatively 6-methoxy-1-aminoindan can be prepared by reductive amination (NaCNBH$_3$ and NH$_4$OAc) of 6-methoxy-indan-1-one to 6-methoxy-indan-1-ylamine. 3-Amino-indan-5-ol can be prepared by using a Friedel-Crafts acylation of an N-protected 3-aminoindan, followed by a Baeyer-Villiger oxidation with subsequent hydrolysis.

These methods for producing starting materials such as 3-amino-indan-5-ol and 6-methoxy-indan-1-ylamine are accompanied by low yields and low reproducibility. Thus, there is a need for reliable processes to produce indanylamine and aminotetralin derivatives in high yields as intermediates to prepare compounds of Formula I, wherein the processes are suitable for industrial production.

SUMMARY OF THE INVENTION

Accordingly, the present invention relates to an improved process for preparing indanyl-(or tetralin)-amines of Formula (II)

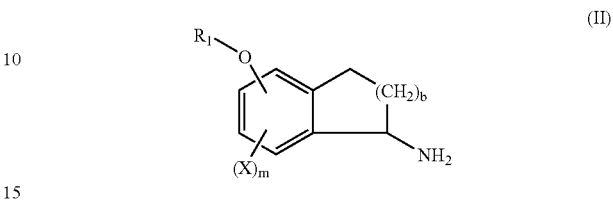

(II)

wherein $R_1$ is a hydrogen atom, an alkyl group, an aryl group, or an acyl group; X is halo, alkyl or alkoxy; m is from 0 to 3; and b is 1 or 2.

In the first step of the process of the present invention, indanylone (or tetralone) oximes (III) are acylated by reaction with an organic anhydride producing indanone (or tetralone) O-acyl oximes (IV). In the second step of the process of the present invention, the O-acyl oximes (IV) are hydrogenated in the presence of a catalyst and organic anhydride to form indanyl-1-(or tetralin)-amides (V). The catalyst is a heterogenous catalyst, for example, Pd/C. In a subsequent step, the amides are hydrolyzed to form indanyl- (or tetralin)-amines of Formula (II).

In a second aspect, the invention relates to novel intermediates, namely, substituted indan-1-one O-acetyl oximes (IV). Both the improved process and novel intermediates are useful in the preparation of therapeutically active compounds used for the treatment of disorders of the central nervous system such as those described by Formula I.

DETAILED DESCRIPTION

The present invention provides a high yield process that can be easily applied at an industrial level for the synthesis of indanylamine or aminotetralin derivatives. The compounds produced by the processes of the current invention are suitable for use as starting materials or intermediates in the production of a variety of pharmaceuticals, for example those presented in Formula I above.

In various embodiments, halo includes fluoro, chloro, bromo, or iodo. Alkyl, alkoxy, etc., include both straight and branched groups; but reference to an individual radical such as "propyl" embraces only the straight chain radical, a branched chain isomer such as "isopropyl" being specifically referred to.

"Alkyl" includes linear alkyls, branched alkyls, and cycloalkyls. Additionally, the alkyls may be substituted with alkoxy, halo, and like substitutents. In some embodiments, alkyl is any one of $C_{1-10}$ alkyl, in other embodiments, alkyl is any one of $C_{1-4}$ alkyl. Example alkyl groups include: $C_{1-4}$ alkyl, such as methyl, ethyl, propyl, isopropyl, butyl, iso-butyl, sec-butyl, tert-butyl; $C_{1-10}$ alkyl, such as methyl, ethyl, propyl, isopropyl, butyl, iso-butyl, sec-butyl, tert-butyl, pentyl, 3-pentyl, hexyl, heptyl, octyl, nonyl and decyl; $(C_{3-12})$ cycloalkyl such as cyclopropyl, cyclobutyl, cyclopentyl, cyclohexyl, cycloheptyl, cyclooctyl, bicyclic, or multi-cyclic substituents, such as of the formulas

"Alkoxy" includes -O-alkyl in which the alkyl is as described above. Example alkoxys include, but are not limited to: methoxy, ethoxy, n-propoxy, n-butoxy, n-pentoxy, hexyloxy, and heptyloxy.

"Acyl" includes —C(=O)R, for example, —C(=O)H, —C(=O)alkyl, - and C(=O)halo, in which the alkyl is as described above. Specific examples of —C(=O)alkyl include, but are not limited to: acetyl, propanoyl, butanoyl, pentanoyl, 4-methylpentanoyl, hexanoyl, or heptanoyl.

"Aryl" includes a phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents. In some embodiments, aryl is a $C_{6-18}$ aryl which is either unsubstituted or substituted. Example aryls include, but are not limited to:phenyl, naphthyl, anthracenyl, phenanthrenyl, fluorenyl, tetrahydronaphthyl, or indanyl.

"Alkylaryl" includes an alkyl-aryl wherein the alkyl and the aryl are as described above. Example alkylaryls include, but are not limited to: benzyl, 2-phenethyl and naphthylenemethyl.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $(C_1-C_{10})$alkyl or $C_{1-10}$alkyl refers to alkyl of one to ten carbon atoms, inclusive, and $(C_1-C_4)$alkyl or $C_{1-4}$alkyl refers to alkyl of one to four carbon atoms, inclusive.

The compounds of the present disclosure are generally named according to the IUPAC nomenclature system. Abbreviations, which are well known to one of ordinary skill in the art, may be used (e.g., "Ph" for phenyl, "Me" for methyl, "Et" for ethyl, "h" for hour or hours, "g" or "gm" for gram(s), "mL" for milliliters, and "rt" for room temperature).

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

The indefinite article "a" or "an" and its corresponding definite article "the" as used herein means at least one, or one or more, unless specified otherwise.

Specific and preferred values listed below for radicals, substituents, and ranges, are for illustration only; they do not exclude other defined values or other values within defined ranges for the radicals and substituents. The compounds of the disclosure include compounds of formulas (I through V) and like compounds having any combination of the values, specific values, more specific values, and preferred values described herein.

The process of the present invention is represented schematically below. The overall process of the invention can be divided into three steps: (1) acylation of the indanone (or tetralin) oxime (III) with an organic anhydride; (2) hydrogenation of the O-acyl indanone (or tetralin) oxime (IV) with a catalyst in the presence of an organic anhydride; and (3) hydrolysis of the amide (V) using an acid generating an indanylamine (II).

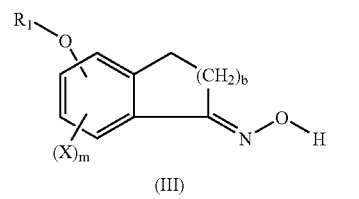

(III)

↓ organic anhydride

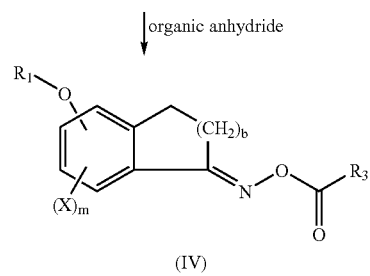

(IV)

↓ organic anhydride
  H₂/catalyst

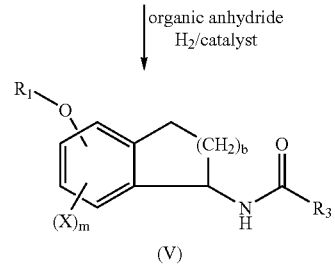

(V)

↓ acid

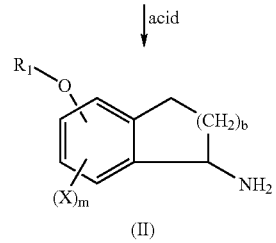

(II)

In Formulas II through V, $R_1$ is hydrogen, alkyl, aryl, or acyl, wherein alkyl, aryl and acyl may be substituted or unsubstituted; X is halo, alkyl or alkoxy; m is from 0 to 3; and b is 1 or 2. When b is 1, the compounds of Formulas II through V may be described as indan derivatives. When b is 2, the compounds of Formulas II through V may be described as tetralin (i.e. dihydronaphthalene) derivatives.

In some embodiments, b is 1. In some embodiments, m is 0. In some embodiments, $R_1$ is any one of $C_{1-4}$ alkyl. In some embodiments, the —$OR_1$ substituent is on the 4, 6 or 7 position of the indan (or tetralin) ring counting from the amino substituted carbon. In some embodiments, —$OR_1$ is 6-methoxy, 7- methoxy, 6-hydroxy, 7-hydroxy, 4-methoxy or 4-hydroxy.

The process of the present invention can be carried out in three separate steps, in which the product of each step is isolated, or alternatively in a one pot reaction, without isolating the product of the first and second steps. In a preferred embodiment, the process is carried out in a one pot reaction.

The first step of the improved process relates to acylation of an indanone or tetralin oxime (III) in the presence of an organic anhydride in an appropriate solvent. In some embodiments, the oxime is a compound of Formula III, wherein $R_1$, X, m, and b are as defined above.

In some embodiments, the organic anhydride is a compound as described by the formla:

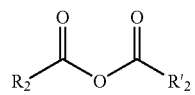

wherein $R_2$ and $R'_2$ are each the same or different and are hydrogen, alkyl, aryl, or alkylaryl, wherein the alkyl, aryl or alkylaryl are unsubstituted or halo substituted. The organic anhydride may be a dialkyl anhydride, a diaryl anhydride or an alkylarylanhydride, and are unsubstituted or halo substituted. In some embodiments, the organic anhydride is acetic anhydride ($R_2$ and $R'_2$ are methyl).

The molar ratio of the organic anhydride to oxime in the first step may be from 1:1 to 5:1. In some embodiments, the molar ratio of organic anhydride to oxime is between about 2:1 to about 5:1. In one embodiment, the molar ratio of organic anhydride to oxime is 3:1. In yet another embodiment, a preferred ratio of organic anhydride to oxime is 1.5:1.

The first step of the process is performed in a suitable solvent. Suitable solvents include, but are not limited to, aprotic non-basic solvents including, ethers, such as tetrahydrofuran (THF), tetrahydropyran, and diethyl ether; organic acid alkyl esters including ethyl acetate; or aromatic hydrocarbons, such as benzene and toluene.

The first step of the process is performed at a temperature range of 0°-80° C. In some embodiments, the temperature range is between about 15°-30° C. In a further embodiment, the temperature is about 20° C. The reaction is carried out over a period of time within the range of 1 to 8 hours. In some embodiments, the reaction time is about 2 hours.

In one embodiment, the O-acyl oxime product (IV) is isolated from the solvent of the first step before performing the second step. In another embodiment, the second step is performed without isolating the O-acyl oxime product (IV) of the first step.

The second step of the improved process relates to a catalytic hydrogenation of the O-acyl oxime product (IV) of the first step in the presence of a catalytic amount of a hydrogenation catalyst, and an organic anhydride in an appropriate solvent.

Suitable hydrogenation catalysts include, but are not limited to heterogeneous catalysts, which include transition metal catalysts comprising transition metals such as Pt, Pd, Ir, Ru, Rh and Ni. Specific examples of suitable heterogeneous catalysts include, but are not limited to: $PtO_2$, Pt/C, Pd/C, Pd/SiO_2, Pd(OH)$_2$/C, Ru/C, Rh/C, and Raney Ni. In one embodiment, the heterogeneous catalyst is Pd/C.

The effective amount of the hydrogenation catalyst may be an amount from 0.1% to 1% w/w in relation to the starting oxime. In one embodiment, the amount of metal catalyst is 0.5% w/w in relation to the indanone or tetralin oxime starting material.

The reaction is performed under hydrogen gas at a pressure of between 0.1 to 15 bars (10 to 1500 kPa), under a temperature range of between 10 to 80° C., for a period of time in the range of 1 to 24 hours. In some embodiments, the hydrogen gas is added to the reaction at a pressure between about 2 to 5 bars (200 to 500 kPa) and in a further embodiment, at about 3 bars (300 kPa). In some embodiments, the reaction temperature is maintained within a range of between about 30-40° C. In one embodiment, the reaction is performed under hydrogen gas pressure of about 4 bars (400 kPa), at a temperature of about 40° C., and for about 4-6 hours.

The second step of the process is performed in a suitable solvent. Suitable solvents include, but are not limited to, aprotic non-basic solvents including ethers, such as tetrahydrofuran (THF), tetrahydropyran, and diethyl ether; organic acid alkyl esters including ethyl acetate; or aromatic hydrocarbons, such as benzene and toluene. In some embodiments, the solvent is the same as used in the first step.

The molar ratio of the organic anhydride in the second step to reactant may be from 1:1 to 5:1; in some embodiments the ratio is 1.5:1. If the first step and the second step are performed in a one pot reaction (i.e. without isolating the product of the first step), the molar ratio of the anhydride to the reactant may be from 2:1 to 5:1, in some embodiments the ratio is 3:1. In yet another embodiment, a preferred ratio of organic anhydride to oxime is 1.5:1.

In one embodiment, the product of step 2 is any one of $C_{1-4}$ alkoxy-indan-1-one O-acetyl oxime. In another embodiment, the product is a methoxy-indan-1-one-O-acetyl oxime. In a further embodiment, the product is a 6-methoxy-indan-1-one O-acetyl oxime. The product may be isolated, if desired, by any conventional means.

The third step of the new process relates to hydrolysis of the amide product of the second step based on methods described in the literature, in an appropriate solvent to obtain indanylamine. (March's Advanced Organic Chemistry; Michael B. Smith and Jerry March, 5th edition, Chapter 10 section 10-11.) One of suitable methods of hydrolysis of the amide product of the second step is using an acid. Hydrochloric acid, sulfuric acid, or other acids may be used as hydrolyzing reagents.

The present invention will be illustrated by the following examples, which should not be considered to limit the scope of the invention in any way.

EXAMPLES

The indanone or tetralone oxime starting materials of the process of the current invention may be prepared from the corresponding ketone derivatives by methods known in the literature. (March's Advanced Organic Chemistry; Michael B. Smith and Jerry March, 5$^{th}$ edition, page 1194.)

For example, an indanone oxime may be prepared by the addition of hydroxylamine to an indanone by the following method. A mixture of 1-indanone with NH$_2$OH.HCl and K$_2$CO$_3$ in a 1:4:4 mole ratio, is refluxed for 3 hours and evaporated to dryness. The residue is extracted with AcOEt and the extract is washed, dried and evaporated to dryness, followed by recrystallization from MeOH. (Oshiro, et al., J. Med. Chem., 34:2004-2013 (1991)).

Suitable indanones and tetralones (dihydro-1-napthalenones) for formation of oxime starting materials include, but are not limited to: 6-methoxy-1-indanones, 4-hydroxy-1-indanones, 7-methoxy-1-tetralones, including indanones and tetralones of the formula below:

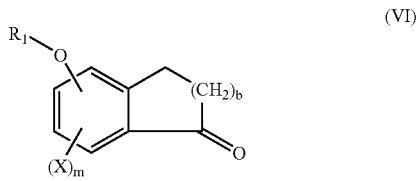

(VI)

wherein R$_1$, X, b and m are as defined herein. Indanones and tetralones are commercially available, for example, from SigmaAldrich, St. Louis, Mo.

Example 1

Acylation process for preparation of 6-methoxy-indan-1-one O-acetyl-oxime [3 to 1 ratio]

6-Methoxy-1-indanone oxime (30 g, 0.169 mol.) was partially dissolved in 180 ml of THF at room temperature. Acetic anhydride (47.9 ml, 0.508 mol) was added to this solution over 15 minutes at 20° C. The reaction mixture was stirred at a temperature between 20-30° C. for 2 hours, then concentrated. A colorless liquid was obtained and solidified into a solid residue. The residue was dissolved in methylene chloride (60 ml) and was washed with water (60 ml) twice. The organic layer was separated from the aqueous layer, dried with MgSO$_4$, filtered, and concentrated to obtain 56 g of a white solid. This product was partially dissolved in methyl tert-butyl ether (MTBE) (60 ml) which was then warmed at 55° C. MTBE (195 ml) was added again slowly to completely dissolve the product. The solution was warmed at reflux temperature for 5 minutes. The solution was cooled to room temperature (20° C.) as the solid crystallized. The solid was filtered and dried under vacuum. 6-methoxy-1-indanone O-acetyl oxime as a white solid (28.8 g) was obtained at a yield of 77.6%.

Example 2

Preparation of N-(6-methoxy-indan-1-yl)-acetamide

6-Methoxy-1-indanone oxime (2 g) was partially dissolved in 20 ml THF. To this solution acetic anhydride (4.4 g) was added over 10 minutes at 15-20° C. The reaction mixture was stirred at 15-20° C. for 2 hours followed by the addition of PtO$_2$ with 40% Pt (14 mg, 1.4% of metal Pt per oxime derivative) to 5 ml of the reaction mixture. The hydrogenation was carried out with a hydrogen pressure of 4 bars (400 kPa) at a temperature between 30-40° C. for 10 hours. The reaction mixture was filtered and then quenched with sodium hydroxide until a pH of about 8-9 was obtained, while maintaining the temperature below 25° C. The aqueous layer was subsequently removed and the organic layer was concentrated to obtain the product, N-(6-methoxy-1-indan-1-yl)-acetamide. The yield was 90%.

Example 3

Preparation of 6-methoxy-indan-1-ylamine

6-Methoxy-indan-1-one oxime (1 kg) was partially dissolved in 6 liters of THF. Acetic anhydride (1.73 kg) was added to the solution over 15 minutes at 20° C. The reaction mixture was stirred between 20-30° C. for 2 hours. To this reaction mixture, Pd/C 5% (0.1 kg, 0.5% of metal Pd/oxime derivative) was added. Hydrogenation was performed with a hydrogen pressure of 3 bars (300 kPa) at a temperature between 30-40° C. over 4-6 hours. The reaction mixture was filtered and concentrated under atmospheric pressure to a volume of 3 liters. The concentrate was warmed to 70° C., then 4 liters of water were added and temperature maintained at 70° C. for 1 hour. The mixture was slowly warmed in a 95° C. bath until evaporation of the solvent was complete. The mixture was cooled to 36° C., 4 liters of methylene chloride were added and the mixture was further cooled to 20° C. The mixture was quenched with an aqueous solution of 30% sodium hydroxide (3.8 kg of solution) to a pH of about 8-9, while maintaining the temperature below 25° C. After removal of the aqueous layer, the organic layer was washed with 1 liter of water and concentrated at atmospheric pressure until the methylene chloride was completely removed. The concentrate was then dissolved in methanol (10 L).

A 36% solution of hydrochloric acid (1.7 kg of solution) was added to the methanolic solution, and the mixture was warmed at 90° C. for 8 hours. After the mixture was cooled to 25° C., a 36% solution of hydrochloric acid (0.86 kg of solution) was added and the mixture was warmed at 90° C. for 7 hours. After cooling to 25° C., another 36% solution of hydrochloric acid (0.29 kg) was added. The mixture was warmed at 90° C. for 6 hours. The mixture was cooled to 25° C. and transferred into a reactor equipped with a scrubber. The mixture was heated to reflux and the methanol was distilled (9 L).

The mixture was cooled to 60° C., followed by addition of water (5 L). Part of the distillate (2 L) was eliminated under pressure at 90° C.

The mixture was cooled to 60° C. and washed with toluene (1 L). The mixture was basified with an aqueous solution of sodium hydroxide to a pH of about 12 to 13 in presence of xylenes at 22° C. The aqueous layer was separated and re-extracted with xylenes (1 L). The organic layer was washed with water (1 L). All organic layers were mixed and concentrated to dryness. The product, 6-methoxy-indan-1-ylamine, was obtained with an overall yield of 65%.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A process of manufacturing a compound of the formula:

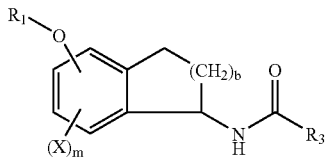

wherein $R_1$ is hydrogen, alkyl, aryl, or acyl; $R_3$ is either $R_2$ or $R'_2$; X is halo, alkyl or alkoxy; m is from 0 to 3; and b is 1 or 2, comprising:

(a) reacting a compound of the formula:

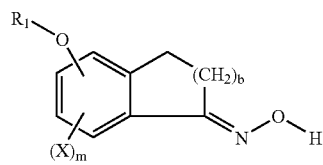

wherein $R_1$, X, m and b are as defined above, with an organic anhydride of the formula:

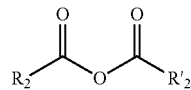

wherein $R_2$ and $R'_2$ are each the same or different and are hydrogen, alkyl, aryl, or alkylaryl, wherein the alkyl, aryl or alkylaryl are unsubstituted or halo substituted, in the presence of a solvent to form a compound of the formula:

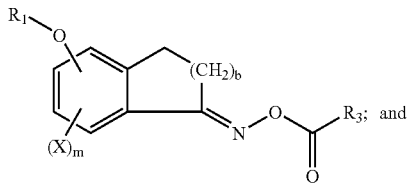

(b) reacting the product of step (a) with hydrogen in the presence of a catalyst and of an organic anhydride as defined in (a) to form the above desired product.

2. The process of claim 1 further comprising:
(c) hydrolyzing the product of (b) to form a compound of the formula:

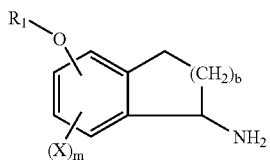

wherein $R_1$, X, m and b are as defined above.

3. The process of claim 2, wherein the product is hydrolyzed using an acid.

4. The process of claim 3, wherein the acid is hydrochloric acid.

5. The process of claim 3, wherein the acid is sulfuric acid.

6. The process of claim 2, wherein $R_1$ is hydrogen, b is 1 and m is 0.

7. The process of claim 2, wherein $R_1$ is methyl, b is 1 and m is 0.

8. The process of claim 7, wherein the —$OR_1$ substituent is on the 4, 6, or 7 position of the indan ring.

9. The process of claim 1, wherein $R_1$, $R_2$ and $R'_2$ are each any one of $C_{1-4}$ alkyl and b is 1.

10. The process of claim 1, wherein $R_1$, $R_2$ and $R'_2$ are methyl, b is 1 and m is 0.

11. The process of claim 10, wherein the —$OR_1$ substituent is on the 4, 6, or 7 position of the indan ring.

12. The process of claim 1, wherein the catalyst is a heterogenous catalyst.

13. The process of claim 12, wherein the heterogenous catalyst is Pd/C.

14. The process of claim 13, wherein the amount of catalyst is between 0.1% and 1% w/w of the starting oxime.

15. The process of claim 1, wherein the solvent is tetrahydrofuran, tetrahydropyran, diethyl ether, ethyl acetate, benzene, or toluene.

16. The process of claim 1, wherein step (a) is carried out at a temperature of 15°-30° C.

17. The process of claim 1, wherein step (b) is carried out at a temperature of 30-40° C.

18. The process of claim 1, wherein the product of step (a) is isolated from the solvent before performing step (b).

19. The process of claim 1, wherein step (b) is performed without isolating the product of step (a) from the solvent.

20. The process of claim 1, wherein the molar ratio of organic anhydride to oxime of step (a) is between 2:1 and 5:1.

21. A process for the preparation of a compound of the formula:

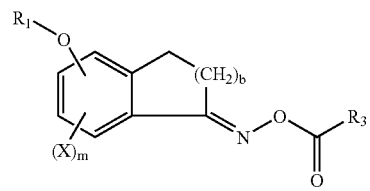

wherein $R_1$ is hydrogen, alkyl, aryl, or acyl; $R_3$ is either $R_2$ or $R'_2$; X is halo, alkyl or alkoxy; m is from 0 to 3; and b is 1 or 2, comprising reacting a compound of the formula:

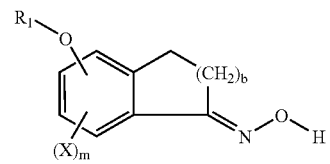

wherein $R_1$, X, and b are as defined above; with an organic anhydride

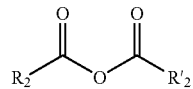

wherein $R_2$ and $R'_2$ are each the same or different and are hydrogen, alkyl, aryl, or alkylaryl, wherein the alkyl, aryl or alkylaryl are unsubstituted or halo substituted, in the presence of a solvent, to form the above desired product.

22. The process of claim 21, wherein b is 1 and $R_1$, $R_2$, and $R'_2$ are each any one of $C_{1-4}$ alkyl.

23. The process of claim 21, wherein $R_1$, $R_2$, and $R'_2$ are methyl, b is 1 and m is 0.

24. The process of claim 23, wherein the —$OR_1$ substituent is on the 4, 6, or 7 position of the indan ring.

25. The process of claim 21, wherein the molar ratio of organic anhydride to oxime is between 1:1 and 5:1.

26. The process of claim 21, wherein the solvent is tetrahydrofuran, tetrahydropyran, diethyl ether, ethyl acetate, benzene, or toluene.

* * * * *